(12) United States Patent
Mbachu et al.

(10) Patent No.: US 7,141,193 B2
(45) Date of Patent: *Nov. 28, 2006

(54) SPECTROSCOPIC MONITORING OF RESIN-APPLICATION PRIOR TO ASSEMBLY OF COMPOSITE WOOD VENEER PRODUCT

(75) Inventors: Reginald A. Mbachu, Eugene, OR (US); Tyler G. Congleton, Eugene, OR (US)

(73) Assignee: Dynea Chemicals Oy, Eugene, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/174,488

(22) Filed: Jul. 6, 2005

(65) Prior Publication Data

US 2005/0241743 A1 Nov. 3, 2005

Related U.S. Application Data

(63) Continuation of application No. 10/797,015, filed on Mar. 11, 2004, now Pat. No. 6,942,826, and a continuation-in-part of application No. 10/338,069, filed on Jan. 7, 2003, now Pat. No. 6,846,447, which is a continuation-in-part of application No. 10/294,296, filed on Nov. 14, 2002, now Pat. No. 6,846,446.

(60) Provisional application No. 60/459,723, filed on Apr. 2, 2003.

(51) Int. Cl.
*B29C 45/76* (2006.01)

(52) U.S. Cl. .................... 264/40.1; 264/406; 264/410; 264/488; 264/492

(58) Field of Classification Search ................ 264/406, 264/40.1
See application file for complete search history.

(56) References Cited

U.S. PATENT DOCUMENTS

| | | | | |
|---|---|---|---|---|
| 6,846,446 B1 * | 1/2005 | Mbachu et al. | ............. | 264/406 |
| 6,846,447 B1 * | 1/2005 | Mbachu et al. | ............. | 264/406 |
| 6,942,826 B1 * | 9/2005 | Mbachu et al. | ............. | 264/40.1 |

* cited by examiner

*Primary Examiner*—Christina Johnson
*Assistant Examiner*—Monica A Huson
(74) *Attorney, Agent, or Firm*—Shanley and Baker, Breiner & Breiner, L.L.C.

(57) ABSTRACT

Method for spectroscopically monitoring resin applied to a planar surface of veneer-wood sheets during travel in an assembly line. Spectroscopic instrumentation for monitoring applied resin is calibrated by measurements of predetermined resin applications to reference-test-samples, so as to provide a pre-determined relationship enabling monitoring of applied resin, during commercial production of a veneer-wood product using the visible light spectrum and near infrared extending to 2500 nm. Monitoring of selected radiation absorbance by the applied resin is carried out by spectroscopic measurement of non-absorbed electromagnetic radiation, as reflected back by the wood-veneer matrix; selected wavelengths are utilized for determining average resin-weight per designated surface area of a sheet. Selecting penetrative wavelengths enables use of multiple types of hardwood and softwood for veneer sheets during in-line production, providing for separate calibration for selected wood type and resin combinations measuring instrumentation.

3 Claims, 5 Drawing Sheets

SPECTROSCOPIC MONITORING OF RESIN-APPLICATION PRIOR TO ASSEMBLY OF COMPOSITE WOOD VENEER PRODUCT

RELATED APPLICATIONS

This is a continuation of application Ser. No. 10/797,015 filed Mar. 11, 2004, now U.S. Pat. No. 6,942,826.

This application claims the benefit of U.S. Provisional Patent Application Ser. No. 60/459,723 filed Apr. 2, 2003; and, is a continuation-in-part of U.S. Ser. No. 10/338,069 (Case 10) filed Jan. 7, 2003 now U.S. Pat. No. 6,846,447, entitled "METHODS FOR MONITORING RESIN-LOADING OF WOOD MATERIALS AND ENGINEERED WOOD PRODUCTS", which is a continuation in part of U.S. Ser. No. 10/294,296 (Case 10) filed Nov. 14, 2002, now U.S. Pat. No. 6,846,446 entitled "NIR SPECTROSCOPIC MONITORING OF RESIN-LOADING DURING ASSEMBLY OF ENGINEERED WOOD PRODUCT".

INTRODUCTION

This invention: relates to quantitative spectroscopic monitoring of resin-application on veneer-wood sheets while moving in-line prior to lay-up assembly of plies for production of engineered composite wood sheets; and, is also concerned with methods for calibrating electromagnetic-radiation spectroscopic instrumentation so as to enable quantitatively monitoring resin as applied to veneer sheets while traveling in-line for lay-up assembly of engineered composite laminated-veneer-panels (LVP) and laminated-veneer-lumber (LVL).

OBJECTS OF THE INVENTION

A primary object is to provide for monitoring of average resin-application on a designated surface area of veneer wood during movement in-line toward lay-up assembly of multiple veneer-wood plies.

A related object provides for calibrating spectroscopic instrumentation utilizing selected electromagnetic-radiation wavelengths which include visible light (VIS) and near-infrared (NIR).

A specific object in calibrating instrumentation is establishing that a linear relationship exists between spectral absorbance data and quantitative resin-application for verifying on-line monitoring of resin-application to be within manufacturing specifications and, also, for optimizing resin usage.

The above objects and other contributions of the invention are considered in more detail in describing the invention in relation to the accompanying drawing.

DETAILED DESCRIPTION OF THE INVENTION

Figure 1:
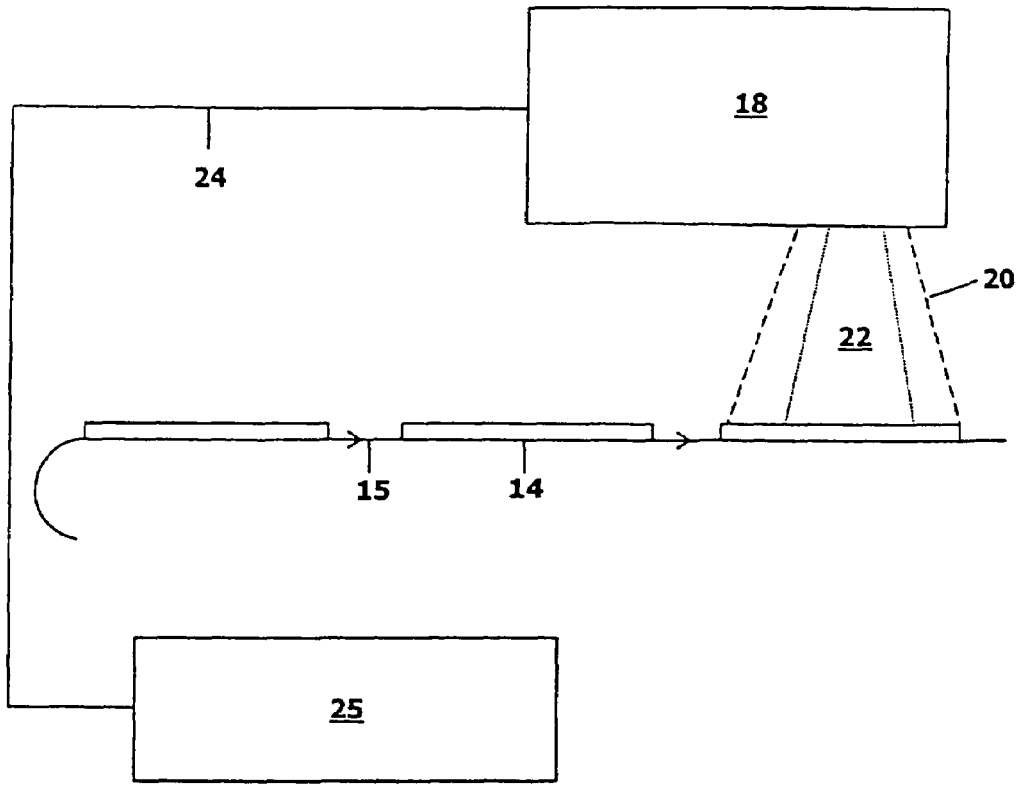
FIG. 1 is a schematic general-arrangement view of in-line apparatus for describing calibration of electromagnetic-radiation spectroscopic instrumentation in accordance with the invention; and, for describing on-line use of calibrated spectroscopic instrumentation for monitoring resin-application during production of wood-veneer product in accordance with the invention.

Differing types of applicators and differing methods for applying adhesive-resin have been developed since the start of the use of resin to assemble veneer wood plies. Those methods for resin application, and the resin applicators, are generally referred to using terminology intended to be descriptive, such as: roll coaters, curtain coaters, extruders, sprayers, etc. Their development and use extend over a period in excess of seven decades, generally seeking to increase production of veneer-wood lay-up in continuous-type lines at particular installations.

Continuous lay-up lines for veneer-wood rely on a "weighing" method for resin application to a sheet. In brief, that method involves: (a) weighing a sample of known area; (b) applying resin; (c) weighing the sample after resin-application; and (d) comparing that result to intended application in terms of weight of resin per unit area. When a setting established for a selected type of applicator provides intended resin weight application rate, the applicator remains on-line, at that setting, for applying resin during a "run" of sheets.

One concern in developing the present technology has been achievement of the named objective of monitoring resin application for maintaining desired resin application while relying on the initially pre-set "weighing" method. Previously a deficiency in resin application during veneer travel might not be detected for an extended period following first occurrence. Further, the "weighing" method can be time consuming, such that: when a pre-set weight for a resin applicator is established the tendency is to rely on that setting for a lay-up of multiple bundles, each with plural plies, during a run.

In such a run, with a "weighing" method pre-setting for the resin applicator, the bundles for assembly can extend to thirty bundles, or more, sometimes extending to a hundred bundles. A discrepancy in resin-application, during such an extended run, could occur for various reasons. For example, unexpected changes in resin application can occur due to a partial blockage along the outlet length of an applicator; or, changes can occur in the resin itself. Such changes can result in non-uniform resin-application to sheets being assembled for subsequent heat and pressure treatment to cure the thermosetting polymeric resin-adhesive. Production of a certain amount of "scrap" veneer-wood product during a run and wasted resin can result, since certain assembled bundles will not be suitable for expected standard uses.

Present innovations are directed to maintaining selected resin application weight with better precision than has been available; and, were developed by (i) analyzing difficulties in extended-surface area resin application during continuing in-line travel for production of veneer-wood product, (ii) working on theoretical concepts which could enable reliable monitoring of resin application on a moving extended-surface-area sheet; (iii) working on those concepts which could enable a non-invasive quantitative monitoring of resin application across a planar veneer-wood surface; (iv) developing monitoring concepts using radiant-energy spectroscopy, (v) providing for calibrating of spectroscopic instrumentation for monitoring resin application over extended planar surface-areas; (vi) selecting wavelengths for combined monitoring of constituents other than resin; and (vii) selecting electromagnetic radiation wavelengths with penetrative properties for differing types of wood.

Pre-setting of a resin applicator by use of the "weighing" method has long been relied on in veneer wood assembly; but, no on-going method for quantitatively monitoring resin-application on a continuous-type assembly line was available in the art, prior to present capabilities which provide for quantitatively measuring resin application to veneer-wood sheets in a timely manner. Present teachings enable an on-going evaluation of surface-applied-resin in a continuous-type assembly line during in-line movement of sheets; such on-line monitoring concepts are carried-out, after resin-application, as a sheet is traveling toward multiple-ply bundling for subsequent resin-curing.

Present spectroscopic resin-monitoring teachings facilitate quality production by enabling a line-operator to make adjustments, responsive to said quantitative measurements, in a timely manner; and, calibrating spectroscopic-instrumentation for use on-line enabling a departure from precision resin application to be promptly discovered and remedied during movement toward lay-up assembly.

On-line monitoring of resin-application, carried out without physically disturbing surface-applied resin, comprises a significant contribution in preparing wood veneer for assembly. Specifically, the invention provides for ongoing "non-invasive" spectroscopic-quantitative monitoring of surface-applied resin during continuing in-line operations.

In accordance with present teachings, spectroscopic-instrumentation is provided so as to position a source, or sources, of electromagnetic radiation wavelengths for coordinated co-action with means for sensing and measuring a response to the irradiation. The source(s) of radiation and the sensor are sometimes referred to in combination, as a "probe". The wavelengths of electromagnetic radiation are selected in one or more ranges for peak absorbance by the applied-resin, and by other constituents, which can also be measured in a manner which helps to sustain desired monitoring accuracy on-line.

Spectral-data for resin application evaluation purposes is based on "absorbance" measurements of the selected wavelengths. That is, quantitative surface-resin-application is determined by measurements of absorption of selected wavelengths by the applied resin. Measuring "absorbed" radiation solves the problem of working with solid veneer wood; and, has significant advantages in enabling the utilization to extend to continuously moving plies on line.

Measuring absorbance also facilitates scientific analyses. That is, measuring absorbance can determine concentration of a chemical constituent of interest; and, that measured absorbance using selected wavelength(s), when expressed mathematically, will be linearly proportional to the quantity of the constituent being investigated.

Selecting electromagnetic wavelengths for peak absorbance by resin; or, by other constituents, such as moisture content of the wood and moisture content of the resin, can also contribute to accurate calibration of instrumentation for on-line spectroscopic monitoring of resin application. Accuracy and timeliness are important to proper on-line monitoring to maintain targeted resin application; and, early detection of an occurring discrepancy can contribute to the ability for a line operator to take steps to minimize, or possibly eliminate, wasted assemblies during an extended run of sheets.

The schematic presentation of FIG. 1 is for describing instrumentation-calibration concepts of the invention which provide for determining quantitative monitoring of resin application during in-line movement of veneer-wood. That is, reference-source test-samples of veneer-wood are moved during calibrating of the spectroscopic equipment, such that the calibration can be used for monitoring resin-application during travel of sheets in continuous-line production operations.

The weight of resin applied to each separate reference-source test-sample, such as 14 of FIG. 1, is pre-determined and accurately pre-established quantitatively. In carrying out calibration, the reference-source test-samples are prepared off-line; preferably in a lab. Reference test-samples can present a uniform surface area and a pre-determined resin-weight per selected area, as pre-established for each sample. As taught herein, those steps in preparing each test sample are carried out in a facility enabling timely provision of individual test samples with a specifically selected resin-weight application.

The test samples are supported for calibration during movement on conveyor 15, which is capable of providing movement of test samples at a selected controlled rate which can be correlated with the rate of movement of sheets in an assembly line on which the instrumentation is to be used for commercial assembly. For calibration purposes, resin-application on each individual reference-source test-sample is pre-established so as to provide for incrementally-differing resin application weights. Commercial production-line resin weights can extend from about twenty-five pounds to about forty pounds of resin per thousand square feet of resin-coated surface area. Incrementally-differing weights per unit area for test-samples are established, for example, to be equivalent to twenty-five, twenty-eight, thirty, thirty-three, thirty-six and forty pounds per thousand square feet of surface area.

Conveyor 15 of FIG. 1 can be a type used during commercial assembly. Conveyor 15 should be selected to be capable of correlating test-sample movement with prospective rates of travel for commercial assembly of veneer-wood sheets; that is, a conveyance for lay-up assembly of veneer wood product while traveling in-line for resin-application in an amount to be established prior to lay-up assembly of multiple-ply bundles. Coordinating rates of movement can involve selecting spectroscopic instrumentation with a faster time for completing calculation of average resin weight applied to a designated surface area. One objective would be to complete a scan by monitoring such an average measurement for each single sheet. That enables resin monitoring to be free of gaps which could tend to throw-off the desired precision of the readings.

In a commercial line, subsequent to assembly, the multiple-ply bundles as assembled are moved toward curing of the applied thermosetting resin of the bundles. Curing is defined as irreversibly changing the properties of a thermosetting resin by chemical reaction; the latter is a form of polymerization; an elevated temperature and pressure can be used during curing with veneer-wood plies.

Curing of the resin is not involved in calibration. Calibration and associated calculation times are concerned with verifying capabilities for spectroscopically monitoring resin application on line. Reference test-samples are prepared with accuracy; and, are prepared in facilities so as to provide for calibration steps to be carried out in a timely-manner; that is: within a selected time subsequent to preparation of the samples which avoids "dry-out" of the resin.

Spectroscopic equipment forming part of probe structure 18 of FIG. 1, as used for calibration purposes, is also used in a continuing assembly line for which it is calibrated. The calibrated instrumentation is positioned on line, subsequent to resin-application, and prior to forming multiple-ply bundles. The spectroscopic instrumentation includes selected sources of radiation wavelengths and radiation sensing means. For example, structure 18 preferably includes a visible-light (VIS) source for illuminating wood-veneer test-samples, and for illuminating selected areas of wood-veneer plies during on-line production. That visible light illumination area is-indicated by beam 20 in FIG. 1. A specific embodiment of structure 18 also includes a near-infra red (NIR) radiation source forming beam 22. Electromagnetic-radiation sources of the invention provides for selecting regions of desired wavelengths in an overall range from about 350 to about 2500 nanometers (nm).

Electromagnetic radiation wavelengths are selected in a range to provide for measuring surface resin and, also, for measuring resin penetration into the wood matrix. Radiation wavelengths are selected to provide for penetration into the surface of various veneer-wood materials, such as poplar, southern yellow pine, and Douglas fir, sufficiently for measuring resin penetration. As taught herein, that contribution is particularly useful for monitoring resin weight on-line; it is important to access actual resin application on differing woods, and, will facilitate verifying calibration of the instrumentation for each separate wood species and resin combination.

Present concepts for quantitative analyses of applied resin analyze concentration of a constituent in solution; that is, the amount of a chemical constituent of interest should be measurable by its effect on a solution. The objective is to find the relationship between test sample observations and the actual concentration of a constituent; finding that relationship is the function of calibrating the measuring instrumentation.

Present tests confirm that resin-absorbance of selected radiation wavelengths is responsive, quantitatively, to applied resin. Also, penetration concepts and selective wavelengths of radiation extend observations to include resin penetrated during on-line operations; and, those observations were further extended to measurements of concentrations of other constituents: such as, moisture-content of the resin and of the wood matrix.

It has been found that, selected ranges of radiation wavelength(s) for absorption by the resin can overlap with wavelengths for other constituents, such as moisture. Non-absorbed radiant energy is "reflected-back" by the matrix. The non-absorbed return-reflected radiation provides the spectral-data for quantitatively evaluating radiation absorbance which is quantitatively responsive to the amount of those constituents; and, more specifically, enables mathematically calculating quantitatively the average applied-resin weight per selected unit of surface area. As above noted, proper measurement should include resin which penetrates the surface of the veneer-wood; the electromagnetic radiation wavelengths are selected to penetrate about two to five millimeters (mm's) into the veneer-wood.

Referring to FIG. 1, non-absorbed radiation of the selected wavelengths by the veneer-wood, with applied resin, traveling on conveyance 15 is return-reflected to probe 18. The return-reflected radiation is directed via fiber-optic cable 24 to instrumentation computer 25 which provides for calculating average resin weight of the resin applied to the surface of each test-sample, including resin absorbed by the wood matrix.

In carrying out instrument calibration, the pre-established resin weight reference-test-samples are prepared for use in a timely manner, with resin accurately applied to each at a selected prescribed weight. Establishing applied resin with accuracy on-line also involves timely utilization of the test-samples such that absorption of radiation can be accurately related to that constituent. The instrumentation is properly calibrated when a linear mathematical relationship is established between (i) the calculated radiation absorbance and (ii) the amount of resin applied to each respective individual test sample. With proper calibration, calculated radiation absorbance follows the incremental increase in resin as applied to individual test samples. That relationship verifies accurate calibration of the spectroscopic instrumentation for use on line, as described in more detail in relationship to later figures, for commercial production.

Wavelengths selected can include those specific to moisture, such as moisture content of the veneer-wood matrix and moisture content of the applied resin. Moisture content absorption of radiation is measured at wavelengths of about 900–1000 nm, 1400–1500 nm; and 1900–2000 nm. Moisture content measurements are included in the computer software computations. The range of electromagnetic radiation spectral data provides for multi-variate measurements by use of partial-least-square (PLS) calculation of the spectral data.

During calibration of the instrumentation, the PLS software analyzes for wavelengths which are most responsive to change in resin levels as applied to the text samples; and, those wavelengths are used, by the software, for calculations during on-line monitoring of resin application. Radiation absorbance, as taught herein, is used for quantitative analyses; and, calibration of instrumentation is carried out by verifying that a linear-relationship exists between radiation absorbance, and the quantity of resin applied, to specified test surface areas; which substantiates proper calibration of on-line spectroscopic instrumentation.

Radiation-wavelength absorbance correlates quantitatively with the known amounts of resin applied on respective test samples; and, use of return-reflected electromagnetic radiation enables measurement of radiation on sheets, absorbance which is essentially opaque for obtaining other types of spectral data. When utilizing partial-least-squares (PLS) for spectroscopic quantitative analyses of spectral-data for each constituent; concentrations and absorbance are regressed simultaneously. The multi variate spectral-data of the resin and other constituent concentrations, such as the moisture-content of the matrix and of the resin, as calculated logarithmically enable verification that a linear-relationship exists between radiation absorbance and quantitative-applied resin. Relying on partial-least-squares (PLS) computation provides for prompt and accurate quantitative analyses of average resin-application per selected unit of surface area; and, proper calibration is verified by the linear-relationship of the pre-established applied-resin with the absorption spectral data.

Figure 2:
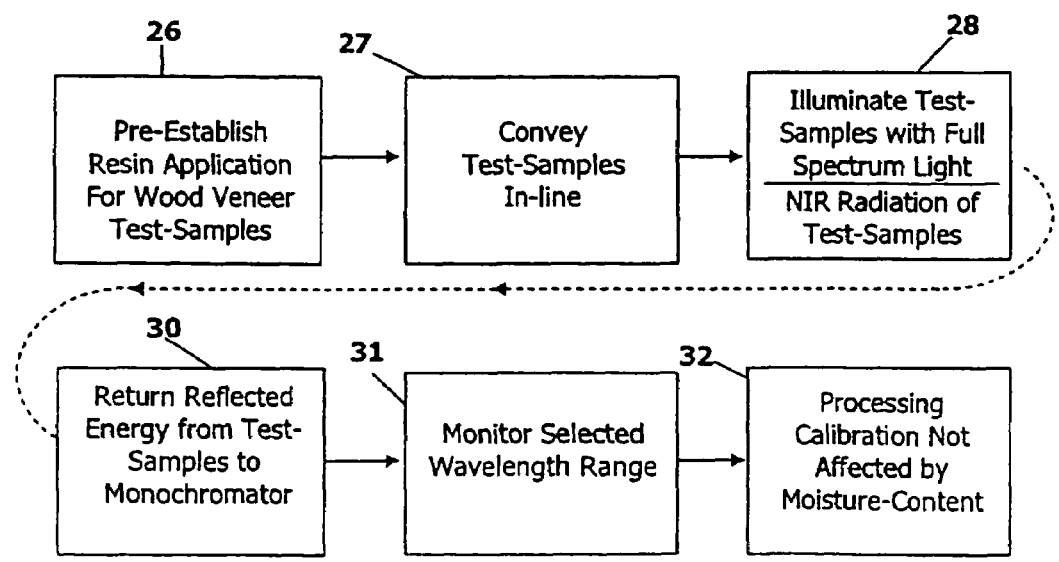
FIG. 2 is a block diagram for describing process steps for calibrating spectroscopic instrumentation in accordance with the invention.

During calibration of the instrumentation, as described in relationship to FIGS. 1 and 2, a thermosetting resin is accurately established by weight and area for each veneer-wood test-sample. Applied-weight levels are established incrementally within a practical range, as set forth earlier. Differing moisture level wood veneer is used in respective test-samples, in order to verify that differing moisture-content of the wood-matrix does not diminish the accuracy in quantitatively measuring resin-application, and avoids any necessity for calibrating the instrumentation for differing moisture contents.

Spectroscopically measuring pre-established resin applications on test samples and verifying the relationship, quantitatively, between the radiation absorbance and the average weight of resin-applied, per selected surface area, provides desired calibration of the spectroscopic instrumentation for measuring absorbed radiation absorbance for monitoring resin application on a continuous-assembly line.

Probe 18 of FIG. 1 establishes a surface area of radiation of about twenty-five square inches. In a specific embodiment, the sensor head is positioned by selecting in a range of about five to about twelve inches above the test sample veneer surface; other dimensions and other energy level sources can be utilized. Also, on a commercial operating-line as later described, plural probe structures, such as 18 of FIG. 1 can be used, each with radiation source(s) of selected wavelengths and sensing means.

The number of probes selected for online use can be based on the width of an elongated sheet while traveling in the direction of its length with applied resin. With a four-foot wide sheet, several probes distributed across sheet width can be utilized in determining whether desired uniformity extends sufficiently across said surface. Using plural spectroscopic instrumentation structures also provides a capability for more accurately and promptly locating, if any discrepancies in resin application, if any occur across a sheet being monitored. During continuing-assembly line measurement of average resin-application, each such spectroscopic-instrumentation structure, at its selected location, monitors an area defined by its projection across the width of the sheet; and, the area monitored extends in a longitudinal direction as established by the relative movement of elongated sheet, with respect to the probe, while traveling toward lay-up.

However, it is not necessary, in practice, to extend width-wise projection of the spectroscopic instrumentation radiation in a manner to contact the lateral edges of a sheet since such lateral edges are normally trimmed after curing. Acceptable accuracy in monitoring resin application, for meeting manufacturing standards across a four-foot wide sheet, for assembly of ply-wood, can be accomplished by selecting multiple probe locations, such as three or four, positioned at selected locations across sheet width. That is, each is separately monitoring resin-application longitudinally of the direction of travel of a sheet. By using four probes of normal proportion, the resultant coverage can directly detect a discrepancy located anywhere over greater than three-quarters of the width of a four-foot wide sheet. Further, each probe establishes an area enabling prompt location for remedy by line operating personnel. Laminated veneer lumber (LVL) is generally laid-up using standard four-foot wide plies, which have been cured and then are cut to size.

In carrying out instrumentation calibration, as set forth in FIG. 2, reference test-samples are prepared with pre-thermosetting resin accurately established by weight and area, at station 26. Such test samples are prepared, as previously described, to enable timely delivery to a conveyance-line for the calibration operation. Such test-samples are positioned for support on a conveyor of the type which conveys wood-veneer sheets in-line, as indicated at station 27 of FIG. 2. Full-spectrum visible-light illumination and NIR radiant energy impingement can be carried-out at stage 28; portions of the visible light spectrum as well as the NIR penetrate the wood matrix for measurement of absorbed resin.

Non-absorbed radiant energy is return-reflected by the matrix of a test sample being carried by the movable support conveyor, as indicated at stage 30 at FIG. 2. The selected wavelength range is monitored at station 31 for return-reflected radiant energy. Calibration for the instrumentation is based on quantitative analyses of pre-established resin-loading of test samples by utilizing a selected wavelength range which is quantitatively responsive to applied resin. As described above, establishing a linear-relationship between the spectral-data absorption response and the amount of resin applied to respective test samples, provides for calibration. At stage 32 of FIG. 2, results of instrumentation calibration verify that measurements are mathematically responsive to the absorbance of the selected wavelengths for respective test samples; and, that the resulting linear-relationship for resin application is independent of moisture content of the matrix or of the resin.

The spectral range and PLS software utilize the entire visible range of light, down to the blue, which is responsive quantitatively to pre-established resin application. Calibrating the instrumentation qualifies its use for monitoring applied-resin on a corresponding assembly line.

In the manufacture of veneer-wood sheets, trees which qualify for making sheets are referred to as "peelers". Referring to the schematic flow-chart of FIG. 3, logs are debarked and cut to length creating "blocks", which determines eventual veneer length along the grain. After cutting, the blocks are sweat-soaked and/or steam heated, in preparation for peeling. The blocks are peeled by a lathe into a "ribbon". The peeled ribbon is then clipped to width into sheets of veneer which now have a length and width. Peeling of layers for forming sheets is carried out at station 34 of FIG. 3. Sheets are cut to desired length and width at station 35; and, the cut sheets are directed to station 36 for feeding into a continuing-type of assembly line. Veneer sheets are assembled, either by hand or machine, as plies (a ply being one veneer sheet layer of an engineered panel) into a proper form to make plywood or LVL.

Figure 3:
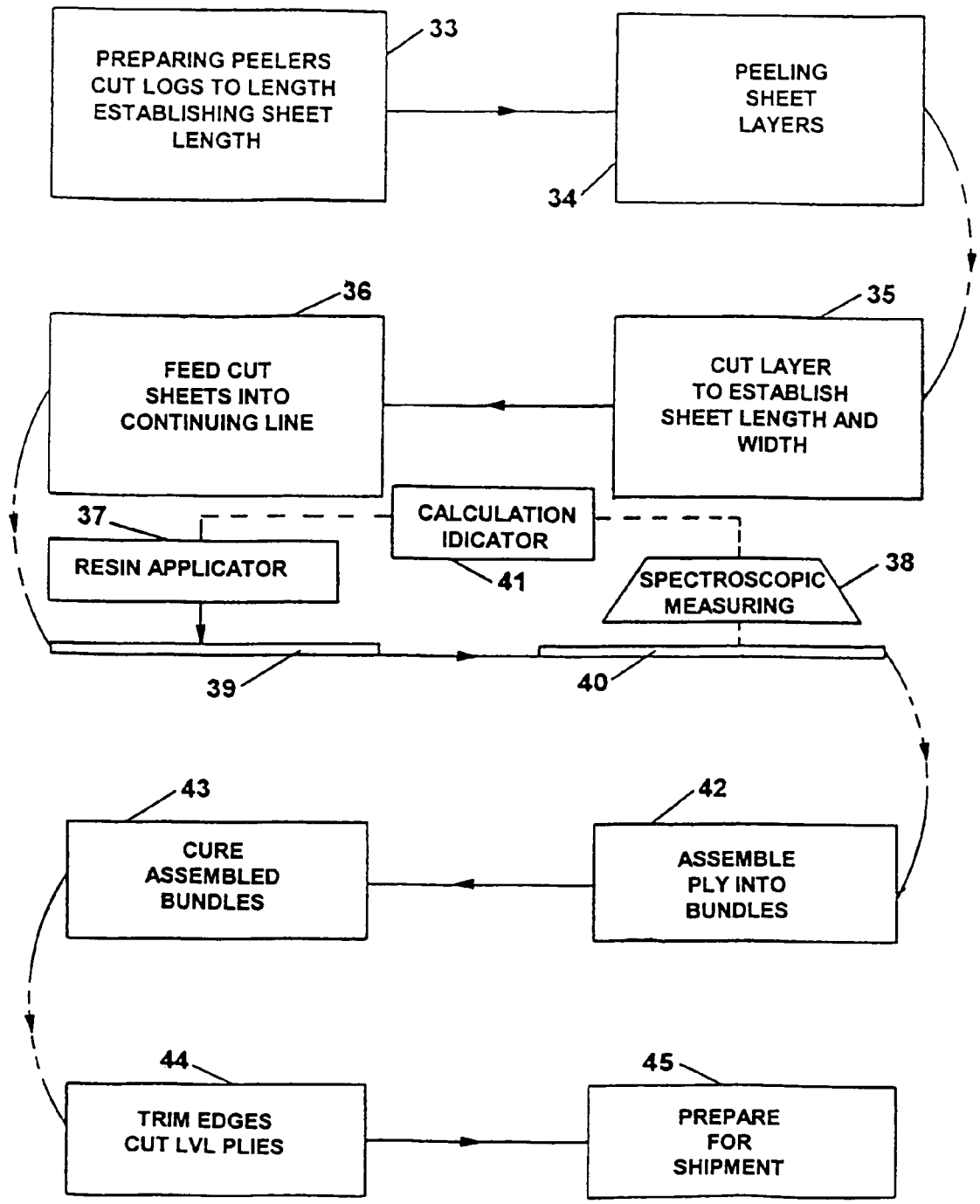
FIG. 3 is a schematic flow-chart presentation for describing the preparation of peeler layers for feeding cut veneer sheets into an assembly line, using calibrated instrumentation for on-line spectroscopic monitoring of resin-application on a surface of cut veneer-wood sheets and for providing an opportunity for a line-operator to sustain desired uniformity of resin-application during production of engineered-composite veneer-wood product.

Resin is applied to a surface of an individual sheet by resin applicator 37 of FIG. 3; and, resin application is monitored spectroscopically by instrumentation 38, while the sheet is traveling in line. Resin application and spectroscopic measuring, respectively at stations 39 and 40, are carried out while sheets are moving in line, in the direction indicated.

A calculation indicator connected as shown schematically in FIG. 3, monitors resin application for alerting line-operating personnel if non-uniformity, or other discrepancy, occurs in a longitudinal travel path covered by the respective spectroscopic-measuring instrumentation being used. Using plural units of spectroscopic instrumentation enables a line-operator to more promptly direct correction(s) to a designated location, widthwise, as may be needed for maintaining desired coating precision.

A pre-selected number of plies with applied resin are assembled at station 42; assembled multiple-ply bundles are subsequently cured, for example by using heat and pressure at station 43. Lateral edges of laminated veneer panels (LVP) can be trimmed, and desired widths for laminated veneer lumber (LVL) can be cut, at station 44. The wood veneer product is prepared for shipment at station 45.

Figure 4:
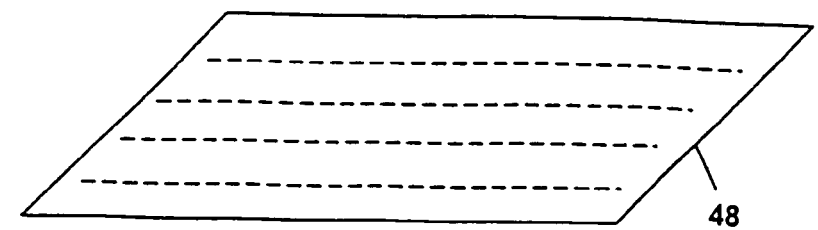
FIG. 4 is a schematic perspective view for describing wood grain-orientation for assembly of veneer-wood plies, with resin-application monitored in accordance with the invention, for desired production of engineered composite-laminated veneer-wood panels (LVP)
Figure 4:
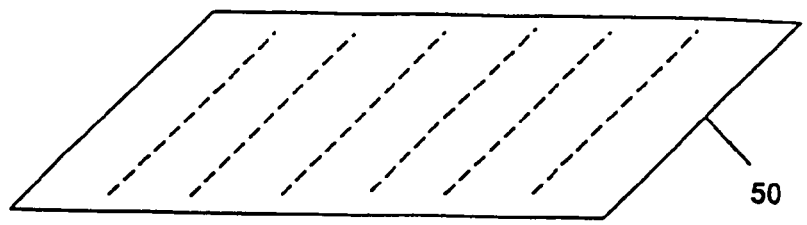
Figure 4:
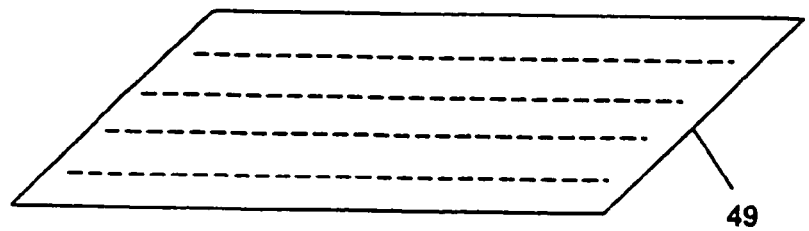
Figure 5:
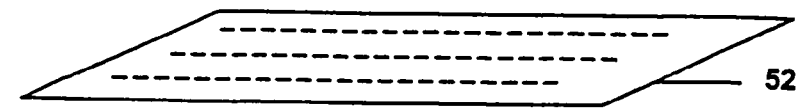
FIG. 5 is a schematic perspective view for describing wood grain-orientation for assembly of veneer-wood plies, with measured resin-application monitored in accordance with the invention, for desired production of engineered composite-laminated veneer lumber (LVL)
Figure 5:
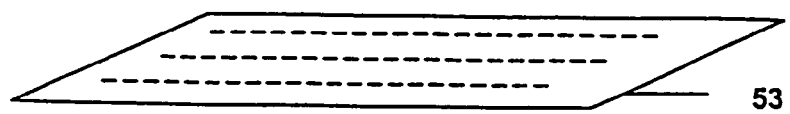
Figure 5:
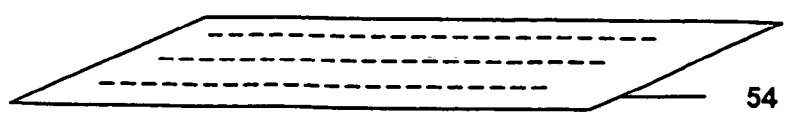
Figure 5:
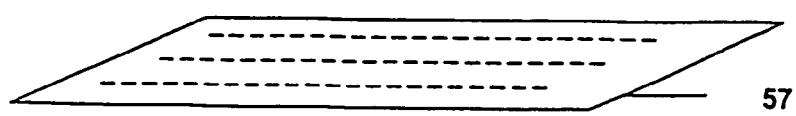

Expanded views of FIGS. 4 and 5 schematically depict wood-grain orientation, respectively, for assembly of laminated veneer-wood panels (plywood) and for assembly of laminated veneer lumber (LVL).

During assembly of plywood (FIG. 4) the orientation of the wood grain for the outer plies 48 and 49 is longitudinal; that is, in the direction of the customary eight foot length of a plywood panel. The wood grain orientation for inner ply 50 is opposite. The total number of plies in plywood can vary from three to about twelve; for greater than three plies, the centrally-located plies alternate in grain orientation. The ability, as disclosed herein, to monitor for targeted resin application as disclosed herein facilitates the manufacture of product which provides uniform bend-resistance in the longitudinal direction, and at right angles to that direction.

The plies for laminate veneer lumber (LVL) shown in FIG. 5 are more significantly elongated than those for plywood; those plies can be cut from four-feet wide assemblies; or, LVL plies can be produced individually to a desired width and assembled to a desired extended length for usage. The grain orientation of all LVL plies such as 52, 53, 54, and 57 shown in FIG. 5 is, as indicated, longitudinal. The number of LVL plies can extend to fifteen, or more. An ability to monitor for uniform average resin loading, as disclosed herein, in combination with the unilateral grain-orientation, provides unique structural support strength for construction uses of LVL.

Calibration concepts for enabling spectroscopic instrumentation to monitor applied resin have been developed for the wood species used to produce veneer wood products. Differing wood species, such as southern yellow pine, poplar, and Douglas fir were tested utilizing radiation wavelengths and steps described above. The wavelength range selected for absorbed energy measurement is monitored by the instrumentation for peak absorption by applied resin. Results verify that each wood species and resin combination is monitored to include that resin absorbed by surface penetration of that resin into a specific species of wood.

Figure 6:
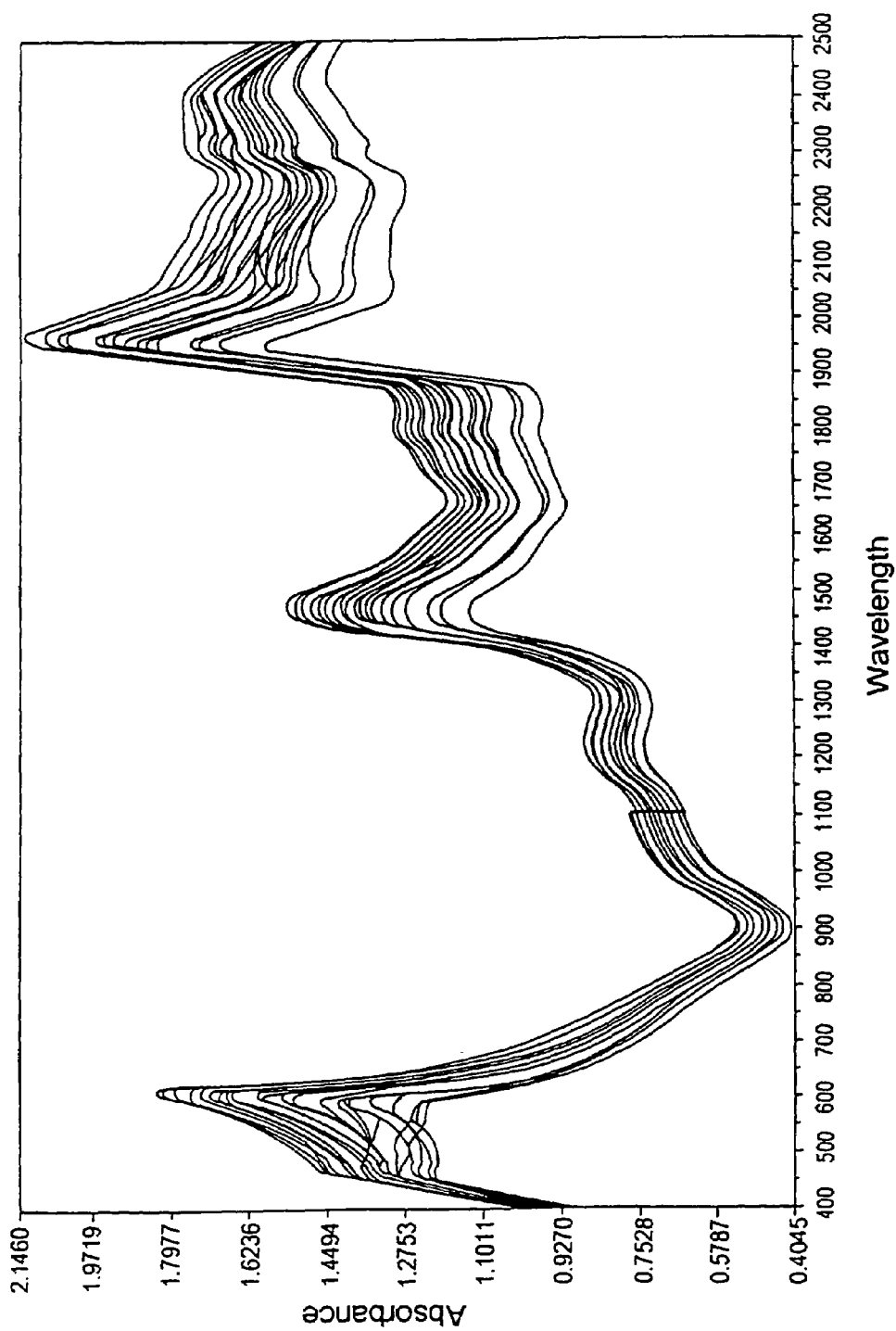
FIG. 6 graphically presents measured spectral data of resin applied to differing species of veneer-wood at selected electromagnetic-radiation wavelengths within about 350 nm to about 2500 nm, utilizing calibrated spectroscopic measuring instrumentation of the invention.

FIG. 6 shows the peak-absorption spectral-data obtained with differing amounts of applied resin utilizing a range of wavelengths from about 400 nm to about 2500 nm. Calibration of the instrumentation is carried out for specific types of resins and for specific types of wood, such as those named, so as to provide calibration of the instrumentation for a harder or softer wood used in assembly. Calibration is carried-out using actual applied-resin by weight per prescribed area. Radiation absorption is measured at wavelengths including the full range of the visible-light spectrum starting at about 400 nm, and NIR through about 2500 nm; which includes absorption wavelengths for moisture contents as part of the calibration.

Figure 7:
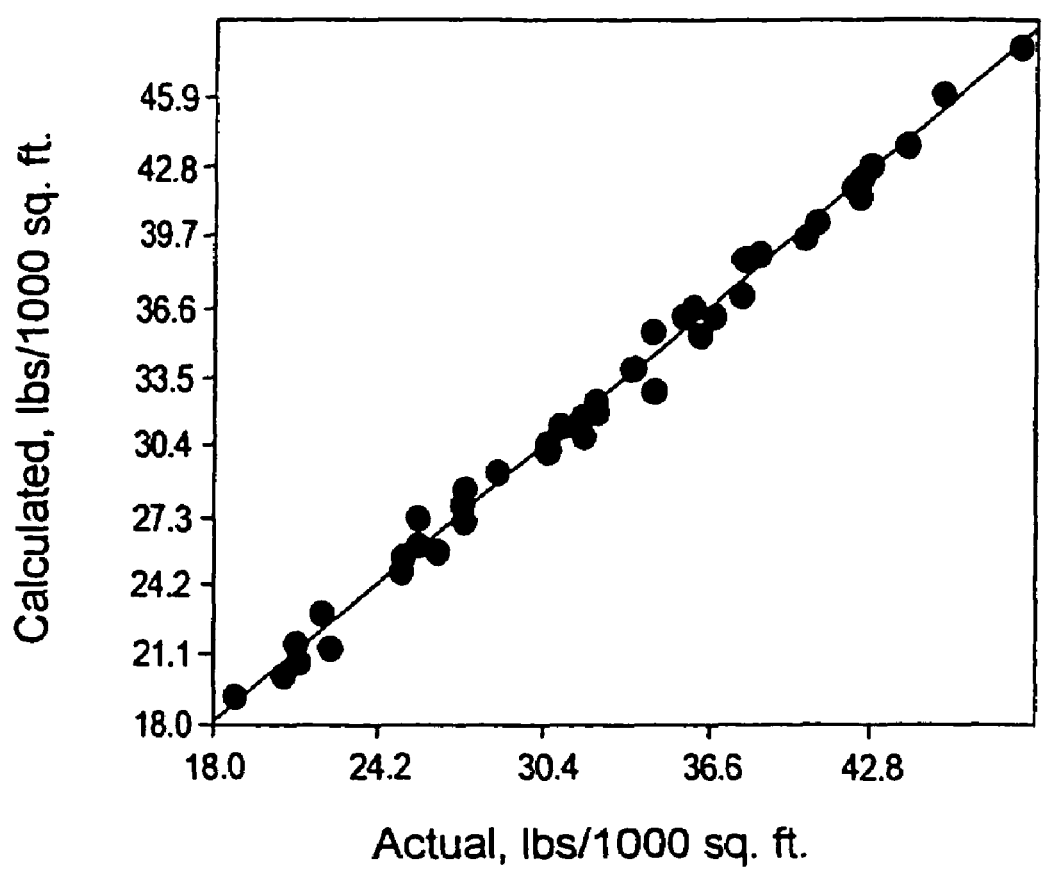
FIG. 7 is a graphical presentation of the results of calibrated spectroscopic instrumentation measurement of average resin application on a surface area of veneer-wood, in which calculation in accordance with the invention establishes a linear-relationship between measured spectral data and quantitative resin-application.

FIG. 7 establishes that a linear-relationship exists between the monitored applied resin weight per 1000 sq. ft. and the actual pre-determined resin weight per 1000 sq. ft. on the test samples, for differing species of veneer-wood including Douglas fir, poplar, and southern yellow pine. Such measurements were made using spectral-absorption data points for all constituents. Partial-Least-Squares (PLS) calculation was used during the calibration because of the complex matrices, including wood species, applied resin, and moisture contents of the resin and the wood. Multiple resin absorption wavelengths were selected for desired accuracy.

Table 1 below relates to correlation coefficients. Use of PLS calculation for calibration involves determining an optimum number of loading vectors (referred to as "regression factors") in the calculations for analyzing spectral data. The term "standard error" is based in part on unit amounts of measured concentrations; the desired accuracy is one (1) pound per thousand square feet of resin application. In the present example, at a regression factor of seven (7), the standard error for calibration is about 0.72 lb/1000 sq. ft. which is slightly better than the acceptable range; and, is acceptable, since seeking lower values trades robustness of the model for precision and accuracy.

For selecting the optimum number of "factors" to use in the calibration model, it is useful to look at the spectral plots of the loadings, which are derived from calculations of second derivative spectra of the samples. The first factor has the highest loading intensity; that intensity decreases for each subsequent regression factor. Table I shows that after seven factors, no further significant variation is presented by additional factors.

TABLE 1

Loadings and weights results of the Example

| Factor | R Squared | Std Error Cal | PRESS | F-Value | Std Err x Val |
|---|---|---|---|---|---|
| Factor 1 | 0.8852 | 2.5821 | 300.0378 | 316.1209 | 2.6415 |
| Factor 2 | 0.8937 | 2.515 | 313.8418 | 168.2178 | 2.7016 |
| Factor 3 | 0.9422 | 1.8782 | 246.9166 | 211.9961 | 2.3963 |
| Factor 4 | 0.9584 | 1.6143 | 237.8684 | 218.9119 | 2.352 |
| Factor 5 | 0.97 | 1.3888 | 309.5573 | 239.5117 | 2.6831 |
| Factor 6 | 0.9869 | 0.9321 | 323.1728 | 450.7694 | 2.7415 |
| Factor 7 | 0.9922 | 0.7265 | 310.1875 | 639.519 | 2.6858 |
| Factor 8 | 0.9958 | 0.5449 | 295.3333 | 998.1 | 2.6207 |
| Factor 9 | 0.9977 | 0.4038 | 294.1875 | 1618.7739 | 2.6156 |
| Factor 10 | 0.9988 | 0.3003 | 302.1217 | 2637.8416 | 2.6507 |
| Factor 11 | 0.9991 | 0.2589 | 305.2063 | 3226.7751 | 2.6642 |
| Factor 12 | 0.9995 | 0.2066 | 305.737 | 4643.8984 | 2.6665 |
| Factor 13 | 0.9997 | 0.166 | 301.4182 | 6644.208 | 2.6476 |
| Factor 14 | 0.9998 | 0.1217 | 302.1944 | 11489.2441 | 2.651 |
| Factor 15 | 0.9999 | 0.0945 | 302.1572 | 17772.7676 | 2.6508 |
| Factor 16 | 1 | 0.0646 | 302.2852 | 35636.2539 | 2.6514 |

The results establish that average resin application can be monitored in a non-invasive manner with desired accuracy under continuing-on-line processing conditions; and, that accurate results are obtained in the absence or the presence of the moisture wavelength bands. Measurement and calculation of average resin loading can be completed for passage of a single sheet by selecting the spectroscopic equipment in correlation with line speed.

Commercial availability of equipment adapted to carrying-out the invention:

Spectroscopic Equipment
   Source:
   Analytical Spectral Devices, Inc. (ASD)
   5335 Sterling Drive, Suite A
   Boulder, Colo. 80301
Instrument Name: Fieldspec PRO.
Sensors (Arranged in Increasing Order of Price)

| Wavelength (nm) | Detector Type |
| --- | --- |
| 350–1050 | Silicon |
| 1000–1800 | Indium-Gallium-Arsenide; single spectrometer |
| 1000–2500 | Indium-Gallium-Arsenide; dual spectrometer |
| 350–2500 | Silicon + Indium-Gallium-Arsenide (photodiode array) |

Software Processing Equipment
 Source: ASD
  For collecting spectra data
 Name: LabSpec PRO, version 7.0
  Source: Thermo Galactic
  For measured Data Processing
 Name: Grams/32 AI
 Materials Used in Carrying Out the Invention:
Resin
 Thermosetting curable resin) is disclosed in co-owned U.S. Pat. No. 5,342,880; specifically:
 Plywood Resin Prefere™ 146303
 Source: Dynea, USA
  1600 Valley River Drive
  Suite 3900
  Eugene, Oreg. 97401

Detailed information on spectroscopic instrumentation, materials, processes, apparatus, calibration of spectroscopic-instrumentation, and monitoring resin applied during continuing on-line assembly have been described so as to enable any person skilled in the art to make and use the invention. That detailed disclosure of test materials, resin, processing spectral data, examples of instrumentation, electromagnetic radiation wavelengths ranges of operation, and other specifics, provide those skilled in the art with a full-disclosure of the invention, and the manner and means for making and using it. Additionally, however, that disclosure places those skilled in the art in a position to make minor changes in one or more of the named specifics, without departing from the disclosed principles of the invention; therefore, it is submitted that any evaluation of valid patent protection should include reference to the scope of the appended claims, interpreted as augmented by the teachings which the above disclosure brings to one skilled in the art to which it pertains.

What is claimed is:

1. Method for calibrating electromagnetic-radiation spectroscopic-instrumentation so as to enable quantitative analyses of curable resin, as applied to a substantially-planar veneer-wood sheet surface area during in-line movement of the sheet toward assembly of multiple-ply bundles for producing engineered-composite wood-veneer product, comprising (A) providing spectroscopic-instrumentation enabling selecting wood-surface penetrative wavelengths of electromagnetic-radiation in a range of about 350 nm to about 2500 nm;

(B) quantitatively pre-establishing pre-determined surface-application of said resin, at a selected level of weight per specified surface area, for individual reference-source wood-veneer test-samples;

(C) supporting said test-samples with pre-established resin-application for movement on a conveyance;

(D) positioning spectroscopic instrumentation providing electromagnetic-radiation in a range of wavelengths including wavelengths absorbed by said resin and capable of penetrating wood-veneer of said test-samples;

(E) controlling rate of movement of said conveyed test-samples with respect to said instrumentation, and coordinating said rate of movement with a selected in-line controlled-rate of movement for lay-up of veneer-wood plies for commercial production of said engineered-composite veneer-wood product;

(F) illuminating a predetermined surface area of said pre-established resin application of said test-samples with visible light (VIS) and simultaneously irradiating with near infra-red (NIR), during said conveyed movement of said test samples relative to said instrumentation, (G) quantitatively measuring radiation absorbance by pre-established resin applications to individual respective test-samples, for calibrating said spectroscopic-instrumentation, during said controlled rate of movement with respect to said instrumentation.

2. The invention of claim 1, further including (H) utilizing spectral-data responsive to absorbance of selected radiation wavelengths, by said pre-established resin-applications on said test-samples, for calibrating said spectroscopic instrumentation for monitoring resin-application, during commercial production of veneer-wood product, by verifying that a linear relationship exists between:

(i) spectroscopically determined absorbance of said selected wavelengths by applied resin, and (ii) said quantitatively pre-established resin-application on respective individual test-samples.

3. The invention of claim 2, including (I) establishing resin-application on said test-samples so as to present an incrementally-progressive quantitative resin-application for veneer-wood of respective test-samples, with said quantitative resin-application being capable of being related to a resin-weight per specified surface area, during commercial production of a veneer-wood product;

(J) receiving spectral-data, in the form of non-absorbed radiant energy, of said selected wavelengths, as reflected back by said conveyed wood-veneer test samples, for spectroscopically determining absorbance of said selected wavelengths by said applied resin, and (K) mathematically calculating radiation absorbance of resin applied to respective test samples, for establishing (i) a linear-relationship between absorbance of said selected wavelengths, and (ii) quantitative resin-application on said individual test-samples for calibrating said spectroscopic instrumentation for use during said commercial production.

* * * * *